United States Patent
Izumi et al.

(10) Patent No.: US 11,557,035 B2
(45) Date of Patent: Jan. 17, 2023

(54) ULTRASONIC DIAGNOSTIC APPARATUS, MEDICAL IMAGE PROCESSING APPARATUS, AND NON-TRANSITORY COMPUTER MEDIUM STORING COMPUTER PROGRAM

(71) Applicant: CANON MEDICAL SYSTEMS CORPORATION, Otawara (JP)

(72) Inventors: Minori Izumi, Shioya (JP); Satoshi Matsunaga, Nasushiobara (JP); Hiroaki Ishikawa, Saitama (JP); Yoshitaka Mine, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 85 days.

(21) Appl. No.: 16/798,614

(22) Filed: Feb. 24, 2020

(65) Prior Publication Data

US 2020/0273168 A1   Aug. 27, 2020

(30) Foreign Application Priority Data

Feb. 26, 2019   (JP) .............................. JP2019-033389

(51) Int. Cl.
*G06T 5/50* (2006.01)
*G06T 7/00* (2017.01)
(Continued)

(52) U.S. Cl.
CPC ............ *G06T 7/0012* (2013.01); *A61B 8/466* (2013.01); *G06T 5/002* (2013.01); *G06T 5/50* (2013.01);
(Continued)

(58) Field of Classification Search
CPC ......... G06T 7/0012; G06T 5/002; G06T 5/50; G06T 2200/08; G06T 2207/10136;
(Continued)

(56) References Cited

U.S. PATENT DOCUMENTS

2015/0181123 A1* 6/2015 Pacurariu ............. H04N 5/3454
                                                        348/208.2
2017/0340311 A1* 11/2017 Shiki ...................... A61B 8/483
(Continued)

FOREIGN PATENT DOCUMENTS

JP       2004-357790 A    12/2004
JP       2004357790 A  *  12/2004
(Continued)

OTHER PUBLICATIONS

Japanese Office Action dated Nov. 15, 2022, issued In Japanese Patent Application No. 2019-033389.

*Primary Examiner* — Bernard Krasnic
(74) *Attorney, Agent, or Firm* — Oblon, McClelland, Maier & Neustadt, L.L.P.

(57) ABSTRACT

The ultrasonic diagnostic apparatus according to the present embodiment includes processing circuitry. The processing circuitry is configured to: acquire multiple position data associated with respective multiple two-dimensional image data of ultrasonic related to multiple cross sections; smooth the acquired multiple position data; and arrange the multiple two-dimensional image data in accordance with the smoothed multiple position data to generate volume data.

10 Claims, 10 Drawing Sheets

(51) Int. Cl.
*A61B 8/00* (2006.01)
*G06T 5/00* (2006.01)

(52) U.S. Cl.
CPC  *G06T 2200/08* (2013.01); *G06T 2207/10136* (2013.01); *G06T 2207/20182* (2013.01); *G06T 2207/20216* (2013.01); *G06T 2207/30004* (2013.01)

(58) Field of Classification Search
CPC . G06T 2207/20182; G06T 2207/20216; G06T 2207/30004; A61B 8/466
See application file for complete search history.

(56) References Cited

U.S. PATENT DOCUMENTS

| | | | |
|---|---|---|---|
| 2018/0092628 A1* | 4/2018 | Mine | A61B 8/463 |
| 2019/0046153 A1* | 2/2019 | Tanaka | A61B 8/5207 |
| 2019/0130564 A1* | 5/2019 | Kawabata | G06K 9/2054 |
| 2020/0043172 A1* | 2/2020 | Ito | G06T 7/0014 |

FOREIGN PATENT DOCUMENTS

| | | | | |
|---|---|---|---|---|
| JP | 2017-213357 A | | 12/2017 | |
| JP | 2017213357 A | * | 12/2017 | |
| WO | WO-2018059837 A1 | * | 4/2018 | A61B 90/37 |

* cited by examiner

3D IMAGE DATA WITH AVERAGING FILTER
(EACH KERNEL INCLUDING THREE COORDINATE ELEMENTS)

3D IMAGE DATA WITH AVERAGING FILTER
(EACH KERNEL INCLUDING FIVE COORDINATE ELEMENTS)

3D IMAGE DATA WITH GAUSSIAN FILTER
(EACH KERNEL INCLUDING FIVE COORDINATE ELEMENTS)

ULTRASONIC DIAGNOSTIC APPARATUS, MEDICAL IMAGE PROCESSING APPARATUS, AND NON-TRANSITORY COMPUTER MEDIUM STORING COMPUTER PROGRAM

CROSS-REFERENCE TO RELATED APPLICATION

This application is based upon and claims the benefit of priority from Japanese Patent Application No. 2019-033389, filed on Feb. 26, 2019, the entire contents of which are incorporated herein by reference.

FIELD

An embodiment as an aspect of the present invention relates to an ultrasonic diagnostic apparatus, a medical image processing apparatus, and a non-transitory computer medium storing computer program.

BACKGROUND

In the medical field, an ultrasonic diagnostic apparatus is used for imaging the inside of a subject using ultrasonic waves generated by multiple transducers of an ultrasonic probe. The ultrasonic diagnostic apparatus causes the ultrasonic probe, which is connected to the ultrasonic diagnostic apparatus, to transmit ultrasonic waves into the subject, generates an echo signal based on a reflected wave, and acquires a desired ultrasonic image by image processing.

The ultrasonic diagnostic apparatus acquires multiple two-dimensional image data with different cross sections and respective multiple position data by moving-operating the ultrasonic probe, and arranges the multiple two-dimensional image data based on the respective multiple position data to generate volume data.

Figure 2A:
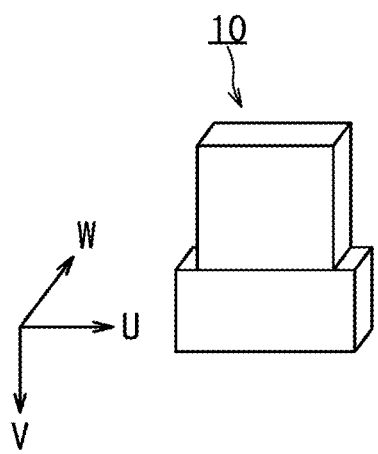
Figure 2B:
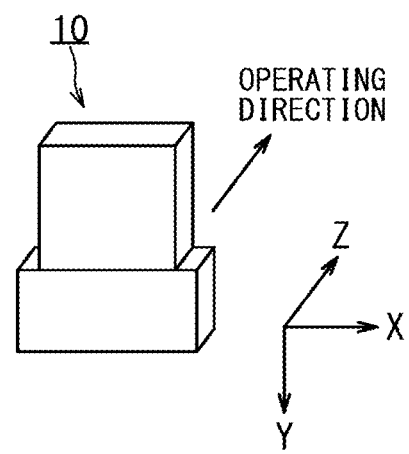

Each of FIGS. 2A and 2B is a diagram for explaining position data of an ultrasonic probe in the ultrasonic diagnostic apparatus according to the present embodiment.

Figure 3:
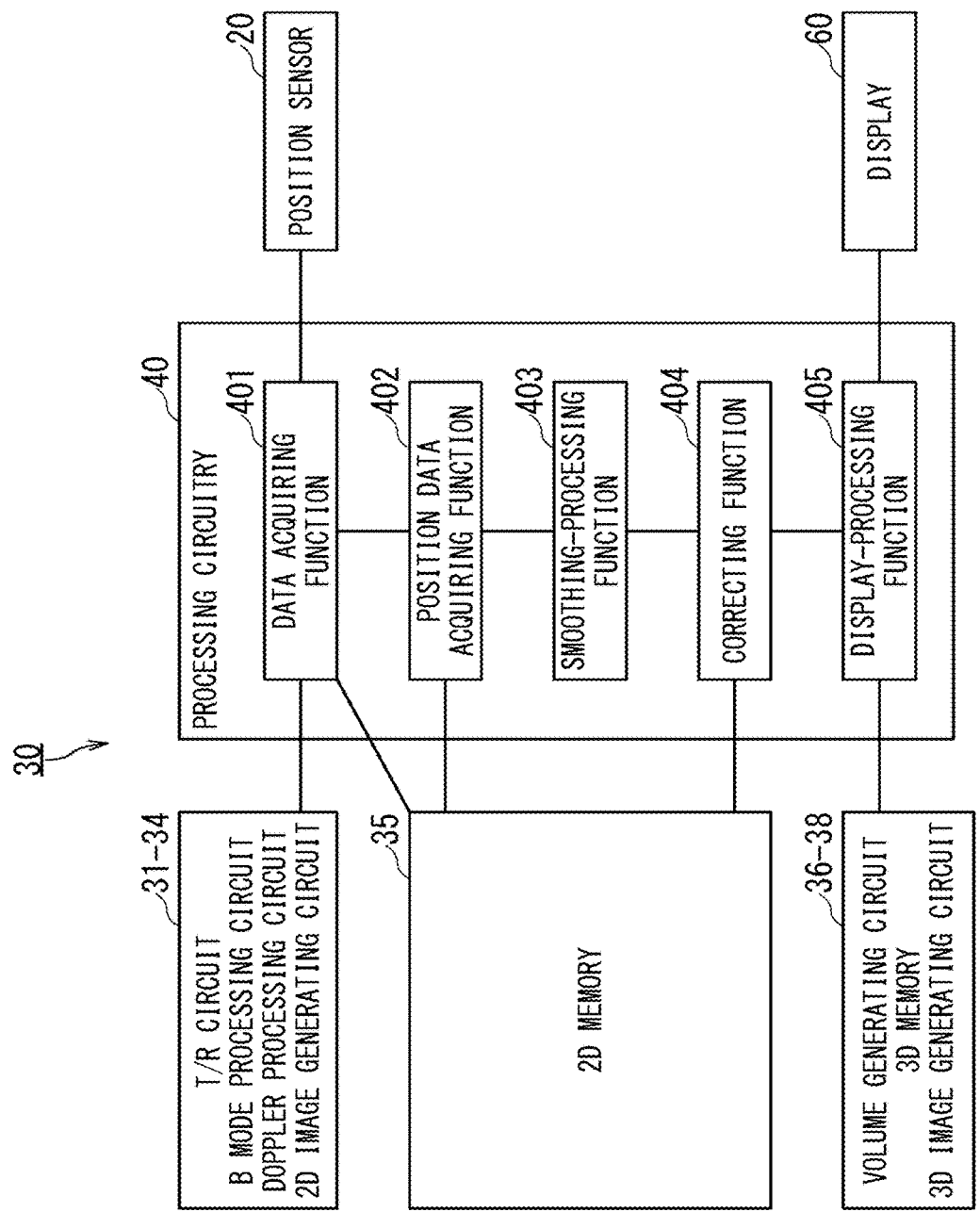

FIG. 3 is a block diagram showing functions of the ultrasonic diagnostic apparatus according to the present embodiment.

Figure 4A:
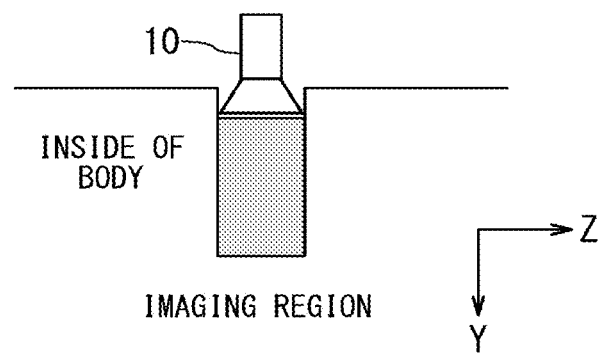
Figure 4B:
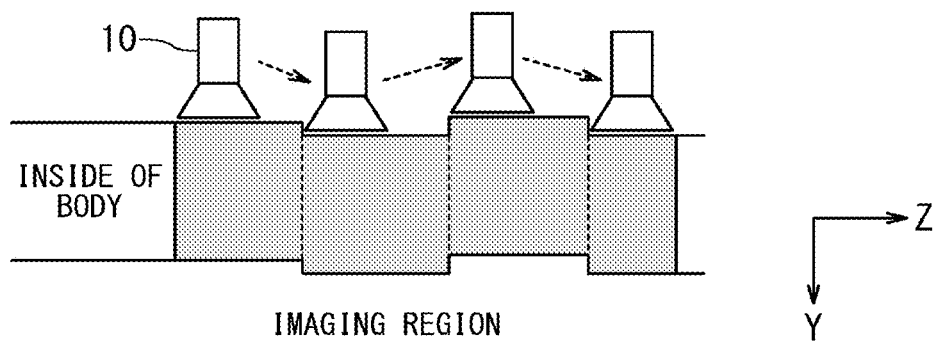

Each of FIGS. 4A and 4B is a diagram showing a relationship between a moving operation of the ultrasonic probe and an imaging region in the ultrasonic diagnostic apparatus according to the present embodiment.

Figure 5:
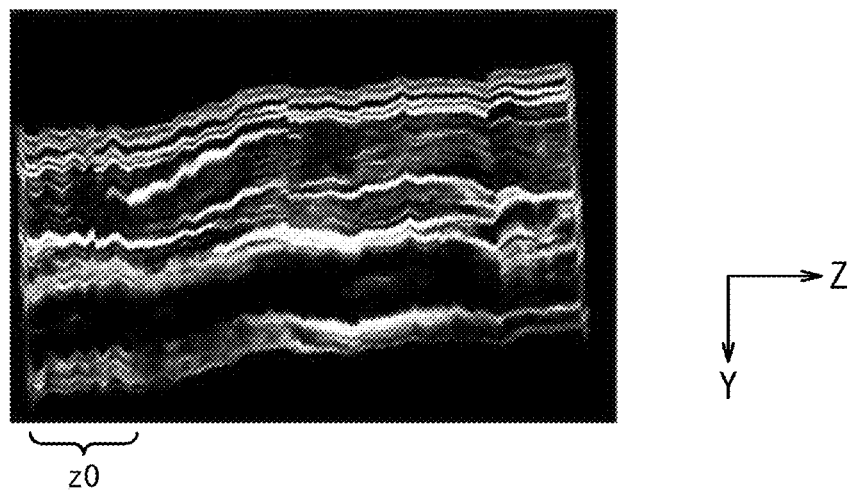

FIG. 5 is a diagram showing 3D image data acquired by changing the imaging region in the ultrasonic diagnostic apparatus according to the present embodiment.

Figure 6:
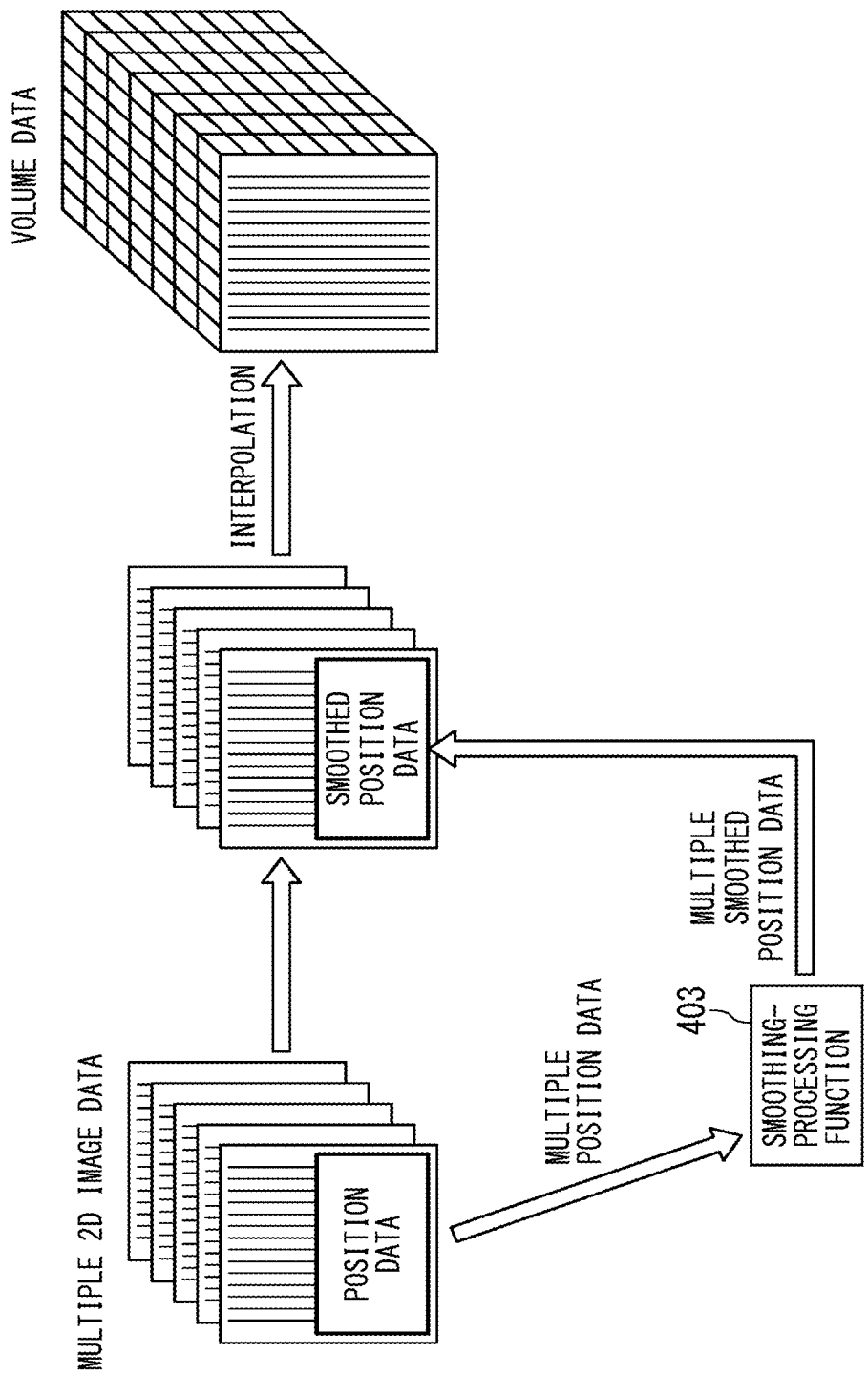

FIG. 6 is a conceptual diagram for explaining an outline of a method of correcting the position data attached to 2D image data in the ultrasonic diagnostic apparatus according to the present embodiment.

Each of FIGS. 7A to 7D is a diagram for explaining a specific method of a smoothing-processing in the ultrasonic diagnostic apparatus according to the present embodiment.

Figure 8:
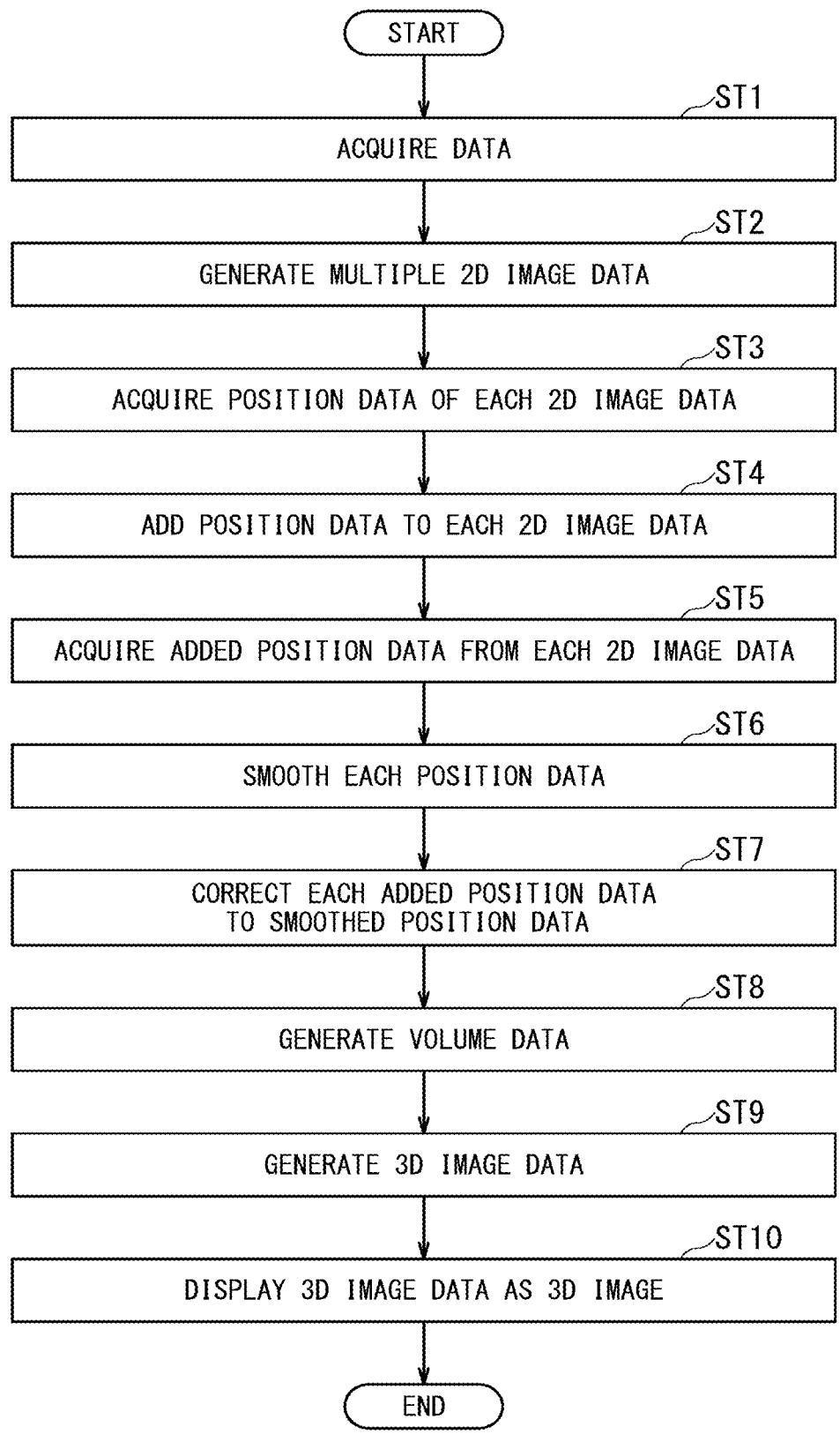

FIG. 8 is a diagram showing the operation of the ultrasonic diagnostic apparatus according to the present embodiment as a flowchart.

Figure 9A:
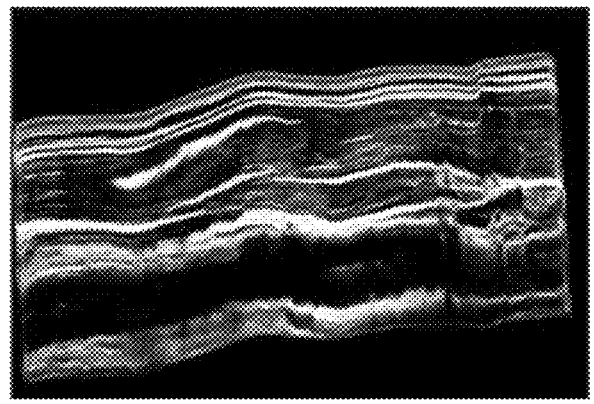
Figure 9A:
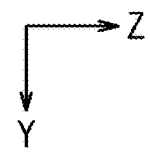
Figure 9B:
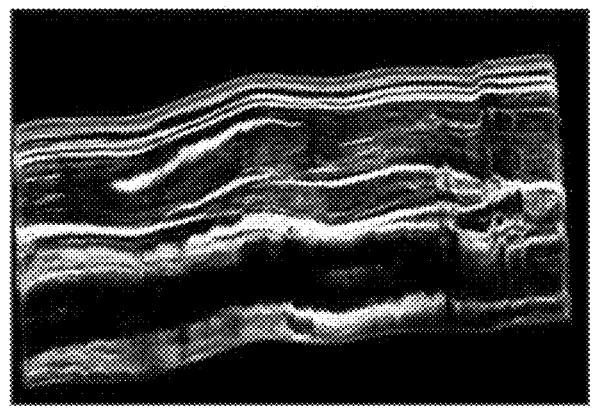
Figure 9B:
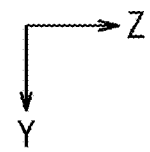
Figure 9C:
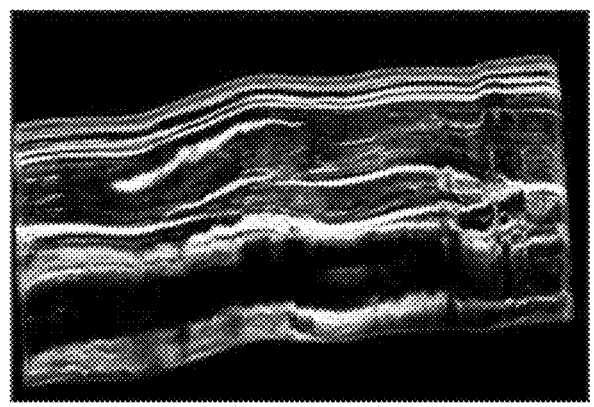
Figure 9C:
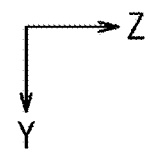

Each of FIGS. 9A to 9C is a diagram showing three-dimensional image data generated based on the smoothed position data in the ultrasonic diagnostic apparatus according to the present embodiment.

Each of FIGS. 10A to 10D is a diagram for explaining a specific method of a smoothing-processing in the ultrasonic diagnostic apparatus according to the present embodiment.

Figure 11:
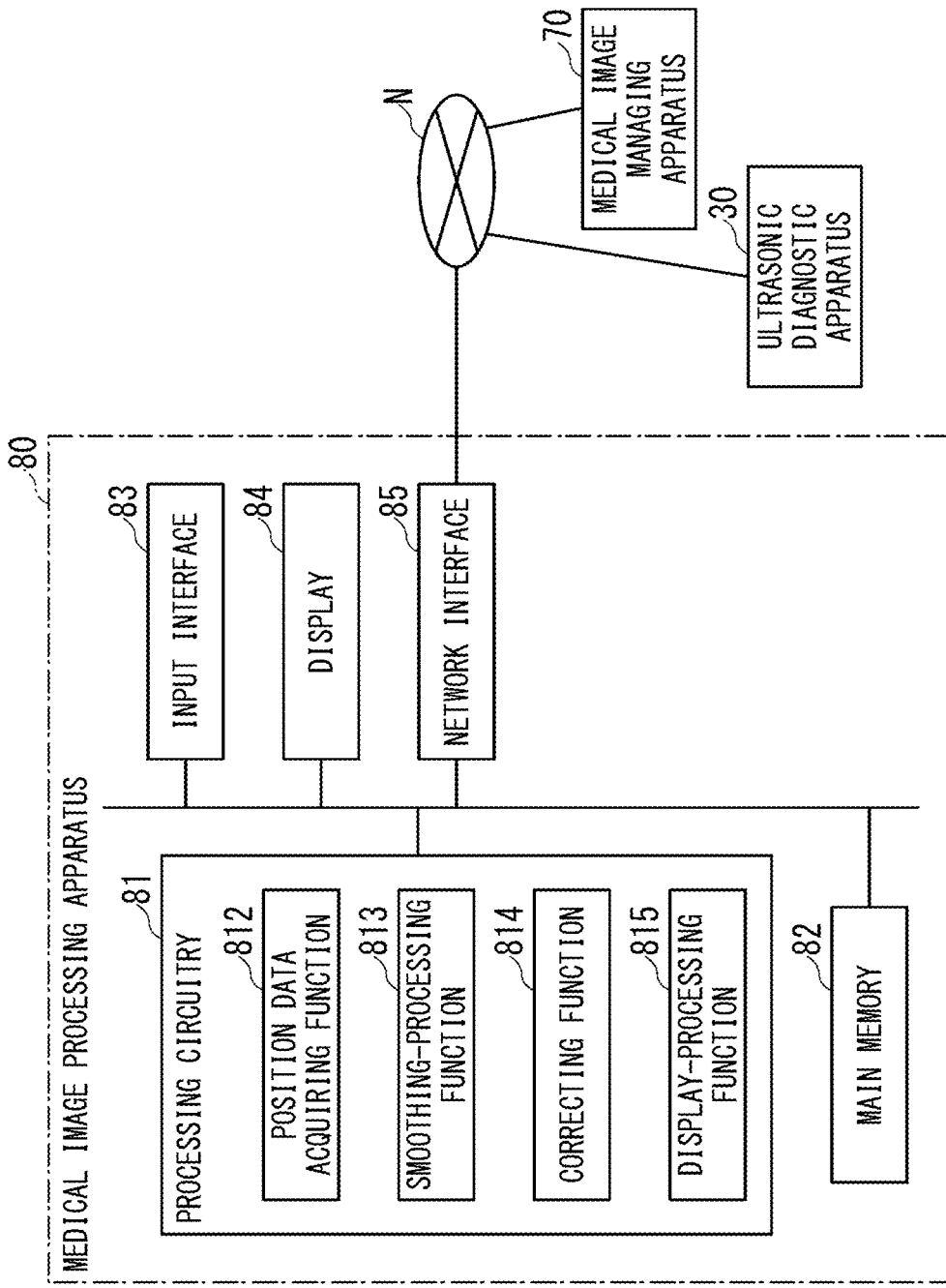

FIG. 11 is a schematic diagram showing a configuration and functions of a medical image processing apparatus according to a present embodiment.

DETAILED DESCRIPTION

An ultrasonic diagnostic apparatus, a medical image processing apparatus, and a non-transitory computer medium storing computer program according to a present embodiment will be described with reference to the accompanying drawings.

The ultrasonic diagnostic apparatus according to the present embodiment includes processing circuitry. The processing circuitry is configured to: acquire multiple position data associated with respective multiple two-dimensional image data of ultrasonic related to multiple cross sections; smooth the acquired multiple position data; and arrange the multiple two-dimensional image data in accordance with the smoothed multiple position data to generate volume data.

1. Ultrasonic Diagnostic Apparatus

Figure 1:
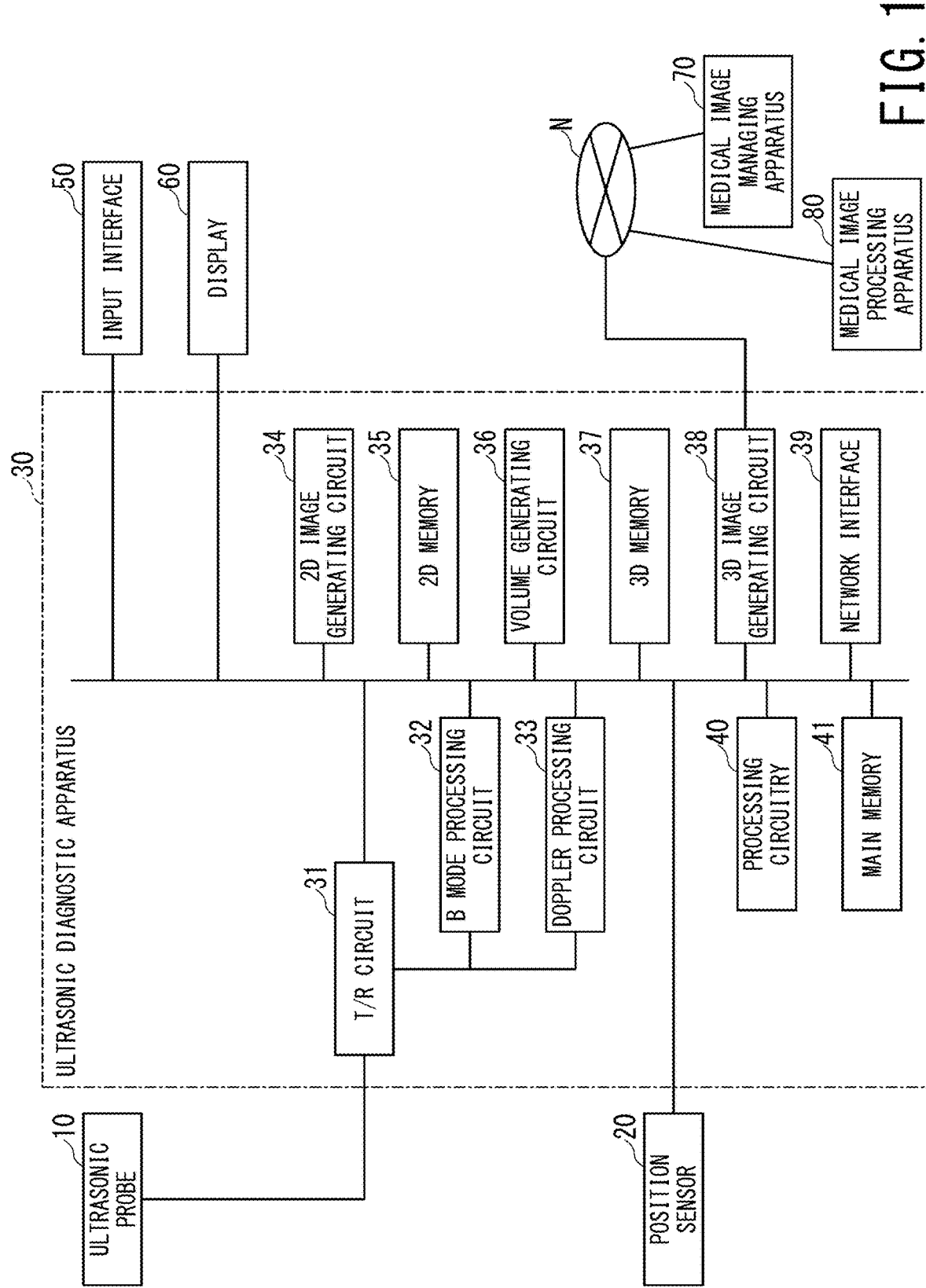
FIG. 1 is a schematic diagram showing a configuration of an ultrasonic diagnostic apparatus according to a present embodiment.

FIG. 1 is a schematic diagram showing a configuration of an ultrasonic diagnostic apparatus according to a present embodiment.

FIG. 1 shows an ultrasonic probe 10, a position sensor 20, an ultrasonic diagnostic apparatus 30 according to the present embodiment, an input interface 50, and a display 60. Note that an apparatus in which at least one of the ultrasonic probe 10, the position sensor 20, the input interface 50, and the display 60 are added to the ultrasonic diagnostic apparatus 30 may be referred to as "ultrasonic diagnostic apparatus". In the following description, a case will be described in which the ultrasonic probe 10, the position sensor 20, the input interface 50, and the display 60 are all provided outside "ultrasonic diagnostic apparatus".

The ultrasonic diagnostic apparatus 30 acquires multiple two-dimensional image data with different cross sections with respective multiple position data by a moving operation of the ultrasonic probe 10 held by an operator, and arranges the multiple two-dimensional image data in accordance with the position data to generate volume data. In the present embodiment, the two-dimensional image data may be data before the scan conversion processing or data after the scan conversion processing. Hereinafter, the former data is called "raw data", and the latter data is called "scan conversion (SC) data".

The ultrasonic probe 10 includes microscopic transducers (piezoelectric elements) on the front surface portion, and transmits and receives ultrasonic waves to a region including a scan target, for example, a region including a lumen. Each transducer is an electroacoustic transducer, and has a function of converting electric pulses into ultrasonic pulses at the time of transmission and converting reflected waves to electric signals (reception signals) at the time of reception. The ultrasonic probe 10 is configured to be small and lightweight, and is connected to the ultrasonic diagnostic apparatus 30 via a cable (or wireless communication).

The ultrasonic probe 10 is classified into types such as a linear type, a convex type, a sector type, etc. depending on differences in scanning system. Further, the ultrasonic probe 10 is classified into a 1D array probe in which transducers are arrayed in a one-dimensional (1D) manner in the azimuth direction, and a 2D array probe in which transducers are arrayed in a two-dimensional (2D) manner in the azimuth direction and in the elevation direction, depending on the array arrangement dimension. The 1D array probe includes a probe in which a small number of transducers are arranged in the elevation direction.

In the present embodiment, when a three-dimensional (3D) scan, that is, a volume scan is executed, the 2D array probe having a scan type such as the linear type, the convex type, the sector type, or the like is used as the ultrasonic probe 10. Alternatively, when the volume scan is executed, the 1D probe having a scan type such as the linear type, the convex type, the sector type and the like and having a mechanism that mechanically oscillates in the elevation direction is used as the ultrasonic probe 10. The latter probe is also called a mechanical 4D probe.

In this case, the effect of suppressing camera shake that tends to occur during the moving operation of the ultrasonic probe, and the effect of suppressing the distortion of the display image due to the pulsation of the blood vessel or the like are remarkable.

The position sensor 20 detects multiple position data of the ultrasonic probe 10 in a chronological order and outputs the multiple position data to the ultrasonic diagnostic apparatus 30. The position sensor 20 is divided into two types, i.e., a sensor that is attached to the ultrasonic probe 10 and a sensor that is provided separately from the ultrasonic probe 10. The latter sensor is an optical sensor. The optical sensor photographs feature points of the ultrasonic probe 10 to be measured, from more than one location. The optical sensor detects each position of the ultrasonic probe 10 based on the principle of triangulation.

The position sensor 20 is attached to the ultrasonic probe 10, detects the position data of the position sensor 20 itself, and outputs the detected position data to the ultrasonic diagnostic apparatus 30. The position data of the position sensor 20 can also be regarded as position data of the ultrasonic probe 10. The position data of the ultrasonic probe 10 includes a coordinate [X, Y, Z] of the ultrasonic probe 10, and a tilt angle [$\theta_x$, $\theta_y$, $\theta_z$] of the ultrasonic probe 10. For example, the magnetic field transmitter (not shown) sequentially transmits triaxial magnetic fields and the position sensor 20 sequentially receives the magnetic fields, thereby making it possible to detect the tilt angle of the ultrasonic probe 10. The position sensor 20 may be a so-called 9-axis sensor including at least one of a triaxial gyroscopic sensor for detecting a triaxial angular velocity in a three-dimensional space, a triaxial acceleration sensor for detecting a triaxial acceleration in a three-dimensional space, and a triaxial geomagnetic sensor for detecting a triaxial terrestrial magnetism in a three-dimensional space.

Each of FIGS. 2A and 2B is a diagram for explaining position data of the ultrasonic probe 10.

FIG. 2A shows three orthogonal directions based on the ultrasonic probe 10, that is, a U-axis direction, a V-axis direction, and a W-axis direction. The U-axis direction is defined by the transducer array direction, that is, an azimuth direction. The V-axis direction is defined by a depth direction, that is, a direction orthogonal to the U-axis direction and the W-axis direction. The W-axis direction is defined by an elevation direction.

FIG. 2B shows three directions in an examination room, that is, an X-axis direction, a Y-axis direction, and a Z-axis direction. The Y-axis direction is defined as a vertical direction in the examination room. The X-axis direction and the Z-axis direction are respectively defined as directions orthogonal to the Y-axis direction.

In the present embodiment, it is described that a case where the ultrasonic probe 10 is arranged on the patient's body surface so that the U-axis direction is parallel to the X-axis direction and the W-axis direction is parallel to the Z-axis direction, and where the ultrasonic probe 10 is moved in the positive or negative direction of the W-axis, that is, in the positive or negative direction (operating direction) of the Z-axis.

Returning to the description of FIG. 1, the ultrasonic diagnostic apparatus 30 includes a transmission/reception (T/R) circuit 31, a B mode processing circuit 32, a Doppler processing circuit 33, a two-dimensional (2D) image generating circuit 34, a two-dimensional (2D) memory 35, a volume generating circuit 36, a three-dimensional (3D) memory 37, a three-dimensional (3D) image generating circuit 38, a network interface 39, processing circuitry 40, and a main memory 41. The circuits 31 to 34, 36, and 38 are configured by application-specific integrated circuits (ASICs) and the like. However, the present invention is not limited to this case, and all or part of the functions of the circuits 31 to 34, 36, and 38 may be realized by the processing circuitry 40 executing a program.

Further, all or part of the members 31 to 41 may be provided in the ultrasonic probe 10.

The T/R circuit 31 has a transmitting circuit and a receiving circuit (not shown). Under the control of the processing circuitry 40, the T/R circuit 31 controls transmission directivity and reception directivity in transmission and reception of ultrasonic waves. The case where the T/R circuit 31 is provided in the ultrasonic diagnostic apparatus 30 will be described, but the T/R circuit 31 may be provided in the ultrasonic probe 10, or may be provided in both of the ultrasonic diagnostic apparatus 30 and the ultrasonic probe 10. The T/R circuit 31 is one example of a transmitter-and-receiver.

The transmitting circuit has a pulse generating circuit, a transmission delay circuit, a pulsar circuit and the like, and supplies a drive signal to ultrasonic transducers. The pulse generating circuit repeatedly generates rate pulses for forming transmission ultrasonic waves at a predetermined rate frequency. The transmission delay circuit converges the ultrasonic waves generated from the ultrasonic transducer of the ultrasonic probe 10 into a beam shape, and gives a delay time for each piezoelectric transducer necessary for determining the transmission directivity to each rate pulse generated by the pulse generating circuit. In addition, the pulsar circuit applies drive pulses to each ultrasonic transducer at a timing based on the rate pulses. The transmission delay circuit arbitrarily adjusts the transmission direction of the ultrasonic beam transmitted from a piezoelectric transducer surface by changing the delay time given to each rate pulse.

The receiving circuit has an amplifier circuit, an analog to digital (A/D) converter, an adder, and the like, and receives the echo signal received by the ultrasonic transducers and performs various processes on the echo signal to generate echo data. The amplifier circuit amplifies the echo signal for each channel, and performs gain correction processing. The A/D converter A/D-converts the gain-corrected echo signal, and gives a delay time necessary for determining the reception directivity to the digital data. The adder adds the echo signal processed by the A/D converter to generate echo data. By the addition processing of the adder, the reflection component from the direction corresponding to the reception directivity of the echo signal is emphasized.

Under the control of the processing circuitry 40, the B mode processing circuit 32 receives the echo data from the receiving circuit, performs logarithmic amplification, envelope detection processing and the like, and thereby generates data (2D or 3D data) which signal intensity is represented by brightness of luminance. This data is an example of the raw data, and is generally called "B mode data". The B mode processing circuit 32 is one example of a B mode processer.

The B mode processing circuit 32 may change the frequency band to be visualized by changing the detection frequency by filtering processing. By using the filtering processing function of the B mode processing circuit 32, harmonic imaging such as the contrast harmonic imaging (CHI) or the tissue harmonic imaging (THI) is performed. That is, the B mode processing circuit 32 may separate the reflected waves from within a subject into which the contrast agent is injected into harmonic data (or sub-frequency data) and fundamental wave data. The harmonic data (or sub-frequency data) corresponds to reflected waves with a harmonic component whose reflection source is the contrast agent (microbubbles or bubbles) in the subject. The fundamental wave data corresponds to reflected waves with a fundamental wave component whose reflection source is tissue in the subject. The B mode processing circuit 32 generates B mode data for generating contrast image data based on the reflected wave data (received signal) of the harmonic component, and generates B mode data for generating fundamental wave image data based on the reflected wave data (received signal) with the fundamental wave component.

In the THI by using the filtering processing function of the B mode processing circuit 32, it is possible to separate harmonic data or sub-frequency data which is reflected wave data (received signal) of a harmonic component from reflected wave data of the subject. Then, the B mode processing circuit 32 generates B mode data for generating tissue image data in which the noise component is removed from the reflected wave data (received signal) of the harmonic component.

When the CHI or THI harmonic imaging is performed, the B mode processing circuit 32 may extract the harmonic component by a method different from the method using the above-described filtering. In harmonic imaging, an imaging method called the amplitude modulation (AM) method, the phase modulation (PM) method or the AM-PM method in which the AM method and the PM method are combined is performed. In the AM method, the PM method, and the AM-PM method, ultrasonic transmission with different amplitudes and phases is performed multiple times on the same scanning line. Thereby, the T/R circuit 31 generates and outputs multiple reflected wave data (received signals) in each scanning line. The B mode processing circuit 32 extracts harmonic components by performing addition/subtraction processing according to the modulation method on the multiple reflected wave data (received signals) of each scanning line. The B mode processing circuit 32 performs envelope detection processing etc. on the reflected wave data (received signal) of the harmonic component to generate B mode data.

For example, when the PM method is performed, the T/R circuit 31 controls the ultrasonic waves of the same amplitude and of reversed-phase polarities, for example (−1, 1), to be transmitted twice by each scanning line under a scan sequence set by the processing circuitry 40. The T/R circuit 31 generates a reception signal based on transmission of "−1" and a reception signal based on transmission of "1". The B mode processing circuit 32 adds these two reception signals. As a result, the fundamental wave component is removed, and a signal in which the second harmonic component mainly remains is generated. Then, the B mode processing circuit 32 performs envelope detection processing and the like on this signal to generate B mode data using THI or CHI.

Alternatively, for example, in the THI, an imaging method using the second harmonic component and a difference tone component included in the received signal has been put to practical use. In the imaging method using the difference tone component, transmission ultrasonic waves are transmitted from the ultrasonic probe 10, and the transmission ultrasonic waves having, for example, a composite waveform in which a first fundamental waves with a center frequency "f1" and a second fundamental waves with a center frequency "f2" larger than the center frequency "f1" are combined. Such a composite waveform is a waveform in which a waveform with the first fundamental waves and a waveform with the second fundamental waves whose phases are adjusted with each other are combined such that the difference tone component with the same polarity as the second harmonic component is generated. The T/R circuit 31 transmits the transmission ultrasonic waves of the composite waveform, for example, twice while inverting the phase. In such a case, for example, the B mode processing circuit 32 removes the fundamental wave component by adding two received signals, and performs an envelope detection process etc. after extracting a harmonic component in which the difference tone component and the second harmonic component are mainly left.

Under the control of the processing circuitry 40, the Doppler processing circuit 33 frequency-analyzes the phase information from the echo data from the receiving circuit, thereby generating data (2D or 2D data) acquired by extracting moving data of moving subject such as average speed, dispersion, power and the like for multiple points. This data is an example of the raw data, and is generally called "Doppler data". In the present embodiment, the moving subject is, for example, blood flow, tissue such as heart wall, or contrast agent. The Doppler processing circuit 33 is one example of a Doppler processer.

Under the control of the processing circuitry 40, the 2D image generating circuit 34 generates multiple 2D image data in a chronological order, i.e., 2D image data in multiple frames, based on the received signals received from the receiving circuit of the T/R circuit 31. Examples of the type of the multiple 2D image data include B mode image data, color mode image data, and application mode image data such as electrography.

In general, a color mode image and an application mode image are displayed in a superimposed manner on a B mode image as a background image. Accordingly, even in the mode for generating these images, B mode image data is also generated. A data region for the color mode image data and the application mode image data is restricted, and thus the data is not suitable for processing to be described later. Accordingly, even when in the mode for generating these images, it is preferable to perform the processing using the B mode image data.

Examples of the form of the multiple 2D image data include the raw data composed of multiple raster data in a scan plane corresponding to a certain time phase, and SC data obtained by performing SC processing on raw data. In the following cases, the 2D image data is the raw data unless otherwise stated.

The 2D memory 35 is a memory circuit including multiple memory cells that correspond to multiple frames and are formed in two axial directions for each frame. The 2D memory 35 stores the multiple raw data, generated by the 2D image generating circuit 34, in a chronological order. Since the ultrasonic probe 10 is manipulated and moved by the operator, the multiple raw data arranged in a chronological order are data located at multiple positions. Time data associated with the acquisition for raster data is attached to raster data, included in each piece of the multiple raw data, by a system timer.

The volume generating circuit 36 arranges the multiple raw data, stored in the 2D memory 35, in the 3D memory 37 in accordance with the corrected position data described later, and performs 3D reconstruction for performing an interpolation-processing as needed, thereby generating volume data in the 3D memory 37. A well-known technique is used as the interpolation-processing method.

The 3D memory 37 is a memory circuit including multiple memory cells in three axial directions (X-axis, Y-axis, and Z-axis directions). The 3D memory 37 stores the volume data generated by the volume generating circuit 36.

The 3D image generating circuit 38 performs a rendering processing on the volume data in order to generate various types of image data for displaying the volume data in the 3D memory 37 on the display 60. The 3D image generating circuit 38 performs the rendering processing such as a multi planar reconstruction (MPR) processing to generate MPR image data from the volume data. In addition, the 3D image generating circuit 38 performs the rendering processing such as a volume rendering (VR) processing to generate image data reflecting 3D information.

The network interface 39 implements various information communication protocols according to the network form. The network interface 39 connects the ultrasonic diagnostic apparatus 30 and other devices such as the external medical image managing apparatus 70 and the medical image processing apparatus 80 according to these various protocols. An electrical connection or the like via an electronic network is applied to this connection. In the present embodiment, the electronic network means an entire information communication network using telecommunications technology. The electronic network includes a wired/wireless hospital backbone local area network (LAN) and the Internet network, as well as a telephone communication line network, an optical fiber communication network, a cable communication network, a satellite communication network, or the like.

Further, the network interface 39 may implement various protocols for non-contact wireless communication. In this case, the ultrasonic diagnostic apparatus 30 can directly transmit/receive data to/from the ultrasonic probe 10, for example, without going through the network. The network interface 39 is one example of a network connector.

The processing circuitry 40 means an ASIC, a programmable logic device, etc. in addition to a dedicated or general purpose central processing unit (CPU), a micro processor unit (MPU), or a graphics processing unit (GPU). The programmable logic device may refer to, for example, a simple programmable logic device (SPLD), a complex programmable logic device (CPLD), or a field programmable gate array (FPGA).

Further, the processing circuitry 40 may be constituted by a single circuit or a combination of independent circuit elements. In the latter case, the main memory 41 may be provided individually for each circuit element, or a single main memory 41 may store programs corresponding to the functions of the circuit elements. The processing circuitry 40 is one example of a processor.

The main memory 41 is constituted by a semiconductor memory element such as a random-access memory (RAM), a flash memory, a hard disk, an optical disk, or the like. The main memory 41 may be constituted by a portable medium such as a universal serial bus (USB) memory and a digital video disk (DVD). The main memory 41 stores various processing programs (including an operating system (OS) and the like besides the application program) used in the processing circuitry 40 and data necessary for executing the programs. In addition, the OS may include a graphical user interface (GUI) which allows the operator to frequently use graphics to display information on the display 60 to the operator and can perform basic operations by the input interface 50. The main memory 41 is one example of a storage.

The input interface 50 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 50 generates an input signal corresponding to the operation and outputs it to the processing circuitry 40. The input interface 50 is one example of an input unit.

The display 60 is constituted by a general display output device such as a liquid crystal display or an organic light emitting diode (OLED) display. The display 60 displays various kinds of information under the control of the processing circuitry 40. The display 60 is one example of a display unit.

FIG. 1 shows the medical image managing apparatus 70 and the medical image processing apparatus 80 which are external devices of the ultrasonic diagnostic apparatus 30. The medical image managing apparatus 70 is, for example, a digital imaging and communications in medicine (DICOM) server, and is connected to a device such as the ultrasonic diagnostic apparatus 30 so that data can be transmitted and received via the network N. The medical image managing apparatus 70 manages a medical image such as an ultrasonic image generated by the ultrasonic diagnostic apparatus 30 as a DICOM file.

The medical image processing apparatus 80 is connected to devices such as the ultrasonic diagnostic apparatus 30 and the medical image managing apparatus 70 so that data is transmitted and received via the network N. An Example of the medical image processing apparatus 80 includes a workstation that performs various image processing on the ultrasonic image generated by the ultrasonic diagnostic apparatus 30 and a portable information processing terminal such as a tablet terminal. It should be noted that the medical image processing apparatus 80 is an offline apparatus and may be an apparatus capable of reading an ultrasonic image generated by the ultrasonic diagnostic apparatus 30 via a portable storage medium.

Subsequently, functions of the ultrasonic diagnostic apparatus 30 will be described.

FIG. 3 is a block diagram showing functions of the ultrasonic diagnostic apparatus 30.

The processing circuitry 40 reads out and executes a computer program stored in a non-transitory computer readable medium such as the main memory 41 or a memory directly incorporated in the processing circuitry 40, thereby realizing a data acquiring function 401, a position data acquiring function 402, a smoothing-processing function 403, a correcting function 404, and a display-processing function 405. The functions 401 to 405 are described as being realized by executing the program. However, all or part of the functions 401 to 405 may be provided in the ultrasonic diagnostic apparatus 30 as a circuit such as an ASIC. Further, all or part of the functions 401 to 405 may be provided in the ultrasonic probe 10.

The data acquiring function 401 has a function of controlling the T/R circuit 31, the B mode processing circuit 32, the Doppler processing circuit 33, and the like to execute an ultrasonic scan, a function of controlling the 2D image generating circuit 34 and the like to generate multiple raw data as 2D image data, and a function of controlling the 2D memory 35 and the like to store the multiple raw data in the 2D memory 35 in association with the respective position data acquired by the position sensor 20. The data acquiring function 401 is an example of a data acquiring unit.

For example, the data acquiring function 401 controls a magnetic field transmitter (not shown) to cause the magnetic field transmitter to transmit a magnetic field, and acquires multiple position data of the ultrasonic probe 10 from the position sensor 20 in time series. The position data includes a coordinate (including elements of XYZ-coordinates) of the ultrasonic probe 10 and a tilt angle (including elements of tilt angles from XYZ-axes) thereof.

The data acquiring function 401 associates each of the multiple raw data generated by the 2D image generating circuit 34 with the respective acquired multiple position data. The data acquiring function 401 compares the multiple time data attached to the respective multiple raw data and the multiple time data attached to the respective multiple position data to associate each of the multiple raw data with appropriate position data, the appropriate position data having a time closest to, immediately before, or immediately after the time of the raw data. In the present embodiment, the time of each of the multiple raw data may be a time attached to the first raster data among multiple raster data constituting each raw data, may be a time attached to the central raster data of the multiple raster data, or may be an average time of the multiple raster data.

The method of adjusting the times of the multiple raw data and the multiple position data is not limited to the above case. For example, by synchronizing the acquisition of the position data by the position sensor 20 with the acquisition of the raw data, the position data may be associated with the corresponding raw data.

The data acquiring function 401 attaches the position data to each of the multiple raw data in order to associate the position data with each of the multiple raw data. For example, the data acquiring function 401 writes the position data in a header or footer of each raw data. The multiple raw data to which the respective multiple position data is attached is stored in the 2D memory 35.

Alternatively, the data acquiring function 401 may write the raw data and the position data in a correspondence table in order to associate the position data with each of the multiple raw data. Hereinafter, a case will be described as an example where the position data is attached to each of the multiple raw data in order to associate the position data with each of the multiple raw data.

Each of FIGS. 4A and 4B is a diagram showing a relationship between the moving operation of the ultrasonic probe 10 and an imaging region.

FIG. 4A shows a concept of an imaging region (scan area) using pressurization by an operator holding the ultrasonic probe 10. FIG. 4B is a diagram showing a concept of an imaging region that fluctuates in the Y-axis direction according to a difference in pressurization during the operation of moving the ultrasonic probe 10 by the operator.

A distorted 3D image is generated and displayed due to the difference in pressurization, as shown in FIG. 4B, during the moving operation of the ultrasonic probe 10 by the operator. The imaging region may fluctuate in the Y-axis direction by movement of the tissue due to respiration or pulsation in addition to the difference in pressurization.

FIG. 5 is a diagram showing 3D image data acquired by changing the imaging region shown in FIG. 4B. FIG. 5 shows 3D image data in a case where a relatively shallow part, for example, a carotid artery, which is liable to cause a change in the imaging region due to a difference in pressurization, is scanned in the B mode.

As shown in FIG. 5, distorted 3D image data is generated due to a difference in pressurization during the moving operation of the ultrasonic probe 10. FIG. 5 shows a case where the difference in pressurization in the Y-axis direction changes as the ultrasonic probe 10 advances in the positive direction of the Z-axis as described in FIG. 4B. In particular, in the range z0 in the Z-axis direction, the imaging region frequently shifts in the Y-axis direction, causing distortion of the entire image.

Therefore, in order to correct the distortion of the 3D image data, the ultrasonic diagnostic apparatus 30 includes the position data acquiring function 402, the smoothing processing function 403, and the correcting function 404.

Returning to the description of FIG. 3, the position data acquiring function 402 includes a function of acquiring, from the 2D memory 35, the multiple position data attached to the respective multiple raw data by the data acquiring function 401. The position data acquiring function 402 is an example of a position data acquiring unit.

The smoothing-processing function 403 includes a function of smoothing the multiple position data acquired by the position data acquiring function 402 in a time direction. For example, the smoothing-processing function 403 acquires each of the multiple position data by averaging the acquired position data and multiple position data associated with respective multiple 2D image data of frames before and after the acquired position data, and thereby smooths the multiple position data. The smoothing-processing function 403 smooths coordinate elements in the three axial directions separately, and the coordinate elements are included in the position data of the ultrasonic probe 10 (shown in FIG. 7 described later). Additionally or alternatively, the smoothing-processing function 403 smooths tilt angles of the ultrasonic probe 10 from three axes separately, the tilt angles being included in the position data of the ultrasonic probe 10 (shown in FIG. 10 described later). The smoothing-processing function 403 is an example of a smoothing-processing unit.

The correcting function 404 includes a function of acquiring the position data before smoothing included in the metadata (for example, patient demographic data) attached to each raw data in the 2D memory 35 to correct (or replace) the acquired position data before smoothing with the position data after smoothing by the smoothing-processing function 403. As a result, each raw data in the 2D memory 35 is attached by corrected position data (hereinafter, referred to as "smoothed position data"). The correcting function 404 is an example of a correcting unit.

FIG. 6 is a conceptual diagram for explaining an outline of a method of correcting the position data attached to the 2D image data (for example, raw data) in the ultrasonic diagnostic apparatus 30.

As shown on the left side of FIG. 6, each position data is attached to raw data. The smoothing-processing function 403 performs a smoothing-processing on each of the multiple position data, and calculates the multiple smoothed position data. Then, the position data attached to each raw data is corrected to the smoothed position data calculated by the smoothing-processing function 403.

Each of FIGS. 7A to 7D is a diagram for explaining a specific method of the smoothing-processing.

Figure 7A:
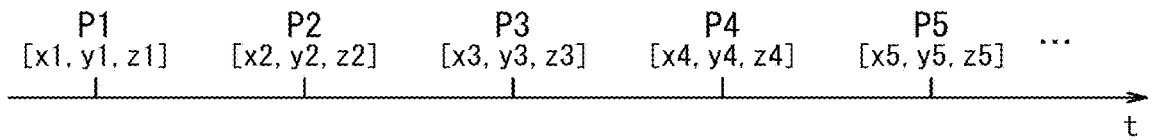

FIG. 7A shows multiple position data P1 to P5 corresponding to the multiple raw data acquired at different times. A coordinate included in position data P1 is [X, Y, Z]=[x1, y1, z1]. A coordinate included in position data P2 is [X, Y, Z]=[x2, y2, z2]. A coordinate included in position data P3 is [X, Y, Z]=[x3, y3, z3]. A coordinate included in position data P4 is [X, Y, Z]=[x4, y4, z4]. A coordinate included in position data P5 is [X, Y, Z]=[x5, y5, z5].

The smoothing-processing function 403 smooths the coordinate elements in the three-axis directions of position data corresponding to each 2D image data in the time direction. For example, the smoothing-processing function 403 smooths the coordinate elements in each axis using a filter averaged in the time direction (shown in FIGS. 7B and 7C). Further, for example, the smoothing-processing function 403 smooths the coordinate elements using a filter that performs weighting in accordance with intervals in the time direction, for example, a Gaussian filter (shown in FIG. 7D). The filter for performing weighting is not limited to a Gaussian filter using a Gaussian function, but may be a filter using other function.

Figure 7B:
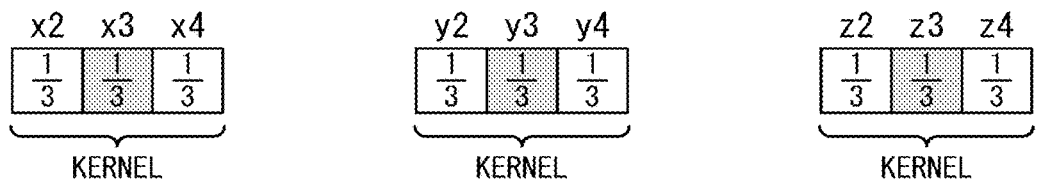

FIG. 7B shows a case where the target position data (gray portion) is "P3". The smoothing-processing function 403 applies a filter for performing simple averaging to the target position data P3 and two position data P2 and P4, thereby acquires new position data P3. The two position data P2 and P4 are respectively associated with two raw data of the frames before and after the position data P3. The smoothing-processing function 403 averages three coordinate elements x2 to x4 in the kernel, thereby smooths the coordinate element x3, which is the X-coordinate of the target position data P3. It should be noted that the smoothing-processing function 403 performs the same processing on a coordinate element y3 that is the Y-coordinate of the target position data P3, and on a coordinate element z3 that is the Z-coordinate thereof. When the target position data is subsequently set to "P4", the smoothing-processing function 403 may use the original position data P3 before applying the filter as the position data of the frame preceding the position data P4. Alternatively, the smoothing-processing function 403 may use the new position data P3 after applying the filter.

Figure 7C:
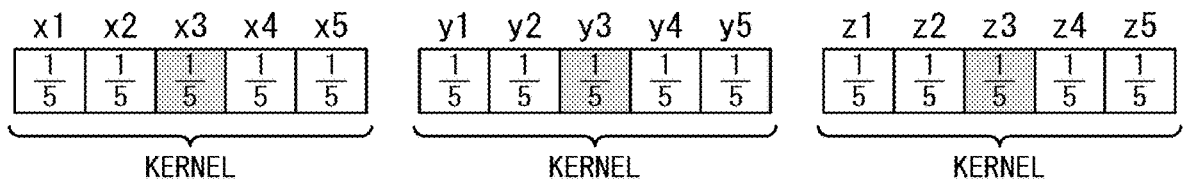

FIG. 7C shows a case where the target position data is "P3". The smoothing-processing function 403 applies a filter for performing simple averaging to the target position data P3 and four position data P1, P2, P4 and P5, thereby acquires new position data P3. The four position data P1, P2, P4 and P5 are respectively associated with four raw data of frames before and after the position data P3. The smoothing-processing function 403 averages five coordinate elements x1 to x5 in the kernel, thereby smooths the coordinate element x3, which is the X-coordinate of the target position data P3. It should be noted that the smoothing-processing function 403 performs the same processing on a coordinate element y3 that is the Y-coordinate of the target position data P3 and on a coordinate element z3 that is the Z-coordinate thereof.

Figure 7D:
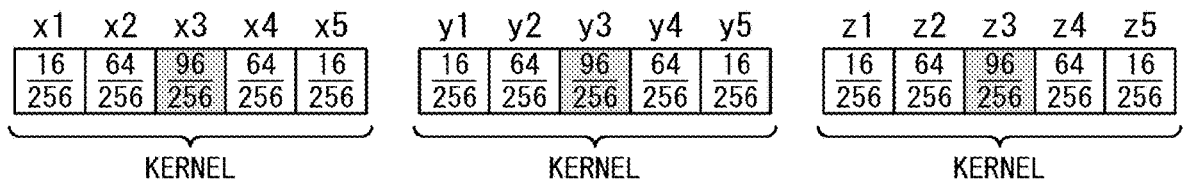

FIG. 7D shows a case where the target position data is "P3". The smoothing-processing function 403 applies a filter for performing weighted averaging to the target position data P3 and four position data P1, P2, P4 and P5 in accordance with intervals from the position data P3, thereby acquires new position data P3. The four position data P1, P2, P4 and P5 are respectively associated with four raw data of frames before and after the position data P3. The smoothing-processing function 403 weights and averages the five coordinate elements x1 to x5 in the kernel, thereby smooths the coordinate element x3, which is the X-coordinate of the target position data P3. It should be noted that the smoothing-processing function 403 performs the same processing on a coordinate element y3 that is the Y-coordinate of the target position data P3 and on a coordinate element z3 that is the Z-coordinate thereof. When the target position data is subsequently set to "P4", the smoothing-processing function 403 may use the original position data P3 before applying the filter as the position data of the frame preceding the position data P4. Alternatively, the smoothing-processing function 403 may use the new position data P3 after applying the filter.

Returning to the description of FIG. 3, the display-processing function 405 includes: a function of generating volume data in the 3D memory 37 based on the multiple raw data in the 2D memory 35 and the multiple smoothed position data by controlling the volume generating circuit 36, the 3D memory 37, and the like; and a function of generating 3D image data for display based on the volume data to display the image data on the display 60 by controlling the 3D image generating circuit 38 and the like. The display-processing function 405 is an example of a display-processing unit.

Subsequently, an operation of the ultrasonic diagnostic apparatus 30 will be described.

FIG. 8 is a diagram showing the operation of the ultrasonic diagnostic apparatus 30 as a flowchart. In FIG. 8, reference numerals in which "ST" is given a number indicate each step in the flowchart.

It should be noted that the smoothing-processing by the smoothing-processing function 403 may be performed after finishing the scan for acquiring multiple 2D image data. Alternatively, the smoothing-processing may be performed on the acquired 2D image data substantially in real time during the scan. Hereinafter, the former case will be described.

A button for starting data acquisition as the input interface 50 is pressed by the operator. Accordingly, the data acquiring function 401 controls the T/R circuit 31 to execute transmission/reception of the ultrasonic wave from the ultrasonic probe 10, and thereby acquires data with the moving operation of the ultrasonic probe 10 (step ST1). The data acquiring function 401 controls the 2D image generating circuit 34 to generate multiple raw data for multiple cross sections based on the data acquired in step ST1 (step ST2). The moving operation of the ultrasonic probe 10 may be performed by an operator holding the ultrasonic probe 10, may be performed using an automatic scan for correcting distortion due to the movement of the patient such as respiratory, or may be performed by a robot arm scan. The robot arm scan is performed for reducing the operator's operation of the ultrasonic probe 10.

The data acquiring function 401 acquires multiple position data of the moved ultrasonic probe 10 from the position sensor 20 as multiple position data of the multiple raw data (step ST3). The data acquiring function 401 adds the position data acquired in step ST3 to each raw data generated in step ST2 (step ST4). The multiple raw data to which the respective multiple position data are attached in step ST4 is stored in the 2D memory 35.

The position data attached to each raw data stored in the 2D memory 35 have been affected by the difference in pressurization during the moving operation of the ultrasonic probe 10 (shown in FIG. 4B).

The position data acquiring function 402 acquires, from the 2D memory 35, each of multiple position data that is the contents of the patient demographic data attached to the raw data in step ST4 (step ST5). The smoothing-processing function 403 smooths the multiple position data acquired in step ST5 in the time direction (step ST6). The method of the smoothing-processing is as described with reference to FIGS. 6 and 7.

The correcting function 404 corrects (or replaces) the position data before smoothing with the smoothed position data in step ST6, and the position data before smoothing is the content of the patient demographic data being attached to each raw data in the 2D memory 35 (step ST7). As a result, each raw data in the 2D memory 35 is attached by the smoothed position data.

The display-processing function 405 controls the volume generating circuit 36, the 3D memory 37, and the like, and arranges each raw data in the 2D memory 35 according to the smoothed position data, performs an interpolation-processing as needed, and generates volume data in the 3D memory 37 (step ST8). The display-processing function 405 controls the 3D image generating circuit 38 and the like to generate 3D image data for display based on the volume data (step ST9), and displays the 3D image data as a 3D image on the display 60 (step ST10).

Each of FIGS. 9A to 9C is a diagram showing 3D image data generated based on the smoothed position data. FIG. 9A shows 3D image data generated based on the smoothed position data acquired by the method described with reference to FIG. 7B. FIG. 9B shows 3D image data generated based on the smoothed position data acquired by the method described with reference to FIG. 7C. FIG. 9C shows 3D image data generated based on the smoothed position data acquired by the method described with reference to FIG. 7D.

Comparing the 3D image data of the carotid artery shown in FIGS. 9A to 9C with the 3D image data of the carotid artery shown in FIG. 5 shows that the fluctuation in the Y-axis direction is small. Comparing the three 3D image data shown in FIGS. 9A to 9C, based on the viewpoint that the fluctuation of the imaging region in the Y-axis direction is eliminated, it is preferable that the degree of smoothing is large. In order to increase the degree of smoothing, the multiple position data being smoothed by using the Gaussian filter is more preferable.

Each position data has been described as being attached to the 2D image data, the present invention is not limited to this case. For example, a correspondence table in which each position data is associated with each 2D image data may be provided. In this case, the smoothing-processing function 403 smooths the position data acquired from the correspondence table and associated with each 2D image data.

According to the ultrasonic diagnostic apparatus 30, the multiple position data of the multiple 2D image data acquired by moving the ultrasonic probe 10 in the Z-axis direction are smoothed in the time direction, and thereby it is possible to correct the fluctuation of the imaging region in the Y-axis direction, which is caused by a change in pressure in the Y-axis direction, when the ultrasonic probe 10 is moved in the Z-axis direction. In the case of a relatively shallow part such as the carotid artery, the effect is greater because the pressing force of the ultrasonic probe 10 appears as image distortion. Thereby, it is possible to display appropriate 3D image data excellent in diagnostic ability. On the other hand, in the case of a relatively deep part such as the abdomen, the effect may be small because the image is not so distorted even if the ultrasonic probe 10 is pressed strongly. However, even in this case of the relatively deep part, the image may be distorted due to body motion caused by respiration, etc. Therefore, the effect is considered to be effective even in the case of the relatively deep part.

2. Modified Example

The case where the smoothing-processing function 403 smooths the coordinates included in the respective multiple position data of the ultrasonic probe 10 in the time direction has been described, the coordinates each including the X-coordinate element, the Y-coordinate element, and the Z-coordinate element. However, it is not limited to this case. For example, the smoothing-processing function 403 may smooth tilt angles included in the respective multiple position data of the ultrasonic probe 10 in the time direction, and the tilt angles each includes tilt angle elements from the X-axis, the Y-axis, and the Z-axis in addition to or as an alternative to the coordinates included in the position data.

Each of FIGS. 10A to 10D is a diagram for explaining a specific method of the smoothing-processing.

Figure 10A:
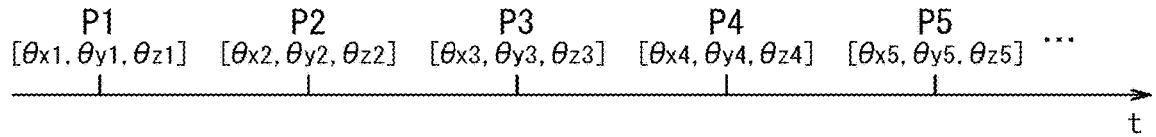

FIG. 10A shows multiple position data P1 to P5 corresponding to the multiple raw data acquired at different times. A tilt angle from each axis included in position data P1 is [θX, θY, θZ]=[θX1, θY1, θZ1]. A tilt angle included in position data P2 is [θX, θY, θZ]=[θX2, θY2, θZ2]. A tilt angle included in position data P3 is [θX, θY, θZ]=[θX3, θY3, θZ3]. A tilt angle included in position data P4 is [θX, θY, θZ]=[θX4 θY4 θZ4]. A tilt angle included in position data P1 is [θX, θY, θZ]=[θX5, θY5, θZ5].

The smoothing-processing function 403 smooths the tilt angle elements from the three-axis directions of position data corresponding to each 2D image data in the time direction. For example, the smoothing-processing function 403 smooths the tilt angle elements in each axis using a filter averaged in the time direction (shown in FIGS. 10B and 10C). Further, for example, the smoothing-processing function 403 smooths the tilt angle elements in each axis using a filter that performs weighting in accordance with intervals in the time direction, for example, a Gaussian filter (shown in FIG. 10D). The filter for performing weighting is not limited to a Gaussian filter using a Gaussian function, but may be a filter using other function.

Figure 10B:
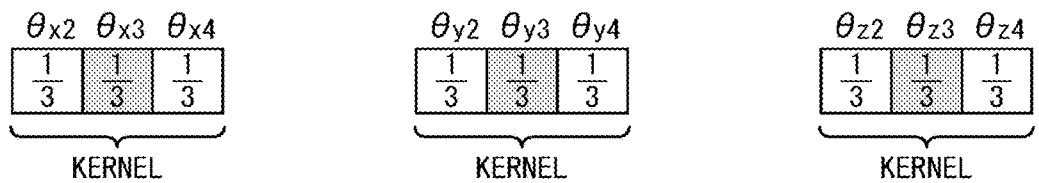

FIG. 10B shows a case where the target position data (gray portion) is "P3". The smoothing-processing function 403 averages three tilt angle elements $\theta_{X2}$ to $\theta_{X4}$ in the kernel, thereby smooths the tilt angle element $\theta_{X3}$, which is the tilt angle from the X-axis of the target position data P3. It should be noted that the smoothing-processing function 403 performs the same processing on a tilt angle element $\theta_{Y3}$ that is the tilt angle from the Y-axis of the target position data P3 and on a tilt angle element $\theta_{Z3}$ that is the tilt angle from the Z-axis thereof.

Figure 10C:
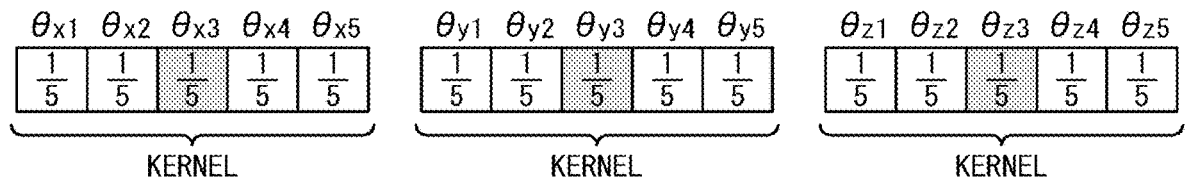

FIG. 10C shows a case where the target position data is "P3". The smoothing-processing function 403 averages five tilt angle elements $\theta_{X1}$ to $\theta_{X5}$ in the kernel, thereby smooths the tilt angle element $\theta_{X3}$, which is the tilt angle from the X-axis of the target position data. It should be noted that the smoothing-processing function 403 performs the same processing on a tilt angle element $\theta_{Y3}$ that is the tilt angle from the Y-axis of the target position data P3, and on a tilt angle element $\theta_{Z3}$ that is the tilt angle from the Z-axis thereof.

Figure 10D:
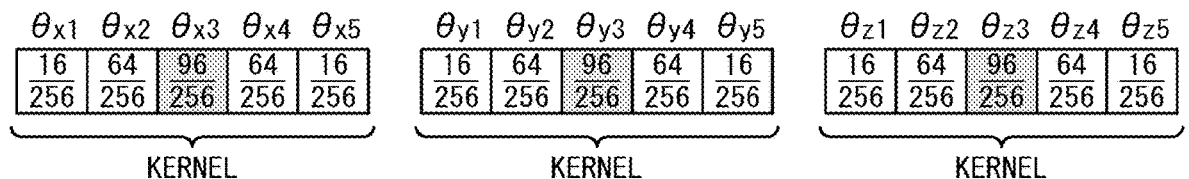

FIG. 10D shows a case where the target position data is "P3". The smoothing-processing function 403 weights and averages the five tilt angle elements $\theta_{X1}$ to $\theta_{X5}$ in the kernel, thereby smooths the tilt angle element $\theta_{X3}$, which is the tilt angle from the X-axis of the target position data P3. It should be noted that the smoothing-processing function 403 performs the same processing on a tilt angle element $\theta_{Y3}$ that is the tilt angle from the Y-axis of the target position data P3 and on a tilt angle element $\theta_{Z3}$ that is the tilt angle from the Z-axis thereof.

According to the modified example of the ultrasonic diagnostic apparatus 30, not only the coordinates of the ultrasonic probe 10 but also the tilt angles thereof are smoothed in the time direction, so that the above-described effect is more remarkable.

3. Medical Image Processing Apparatus

FIG. 11 is a schematic diagram showing a configuration and functions of a medical image processing apparatus according to a present embodiment.

FIG. 11 shows a medical image processing apparatus 80 according to the present embodiment. The medical image processing apparatus 80 is a medical image managing apparatus (image server), a workstation, a medical interpretation terminal, or the like, and is provided on a medical image system connected via a network. The medical image processing apparatus 80 may be an offline apparatus.

The medical image processing apparatus 80 includes processing circuitry 81, a main memory 82, an input interface 83, a display 84, and a network interface 85. The processing circuitry 81, the main memory 82, the input interface 83, the display 84, and the network interface 85 have the same configuration as the processing circuitry 40, the main memory 41, the input interface 50, the display 60, and the network interface 39 shown in FIG. 1, respectively. Therefore, those explanations are omitted.

The processing circuitry 81 reads out and executes a computer program stored in a non-transitory computer readable medium such as the main memory 82 or a memory directly incorporated in the processing circuitry 81, thereby realizing a position data acquiring function 812, a smoothing-processing function 813, a correcting function 814, and a display-processing function 815. The functions 812 to 815 are described as being realized by executing the program. However, all or part of the functions 812 to 815 may be provided in the medical image processing apparatus 80 as a circuit such as an ASIC. Further, the functions 812 to 815 may be configured to be performed in a distributed manner by multiple devices on the medical image system.

The main memory 82 stores the multiple 2D image data (for example, raw data) and the multiple position data, both acquired by the data acquiring function 401 (shown in FIG. 3) from the medical image managing apparatus 70 or the ultrasonic diagnostic apparatus 30 via the network interface 85.

The position data acquiring function 812 includes a function of acquiring multiple position data attached to the multiple raw data from the main memory 82. The position data acquiring function 812 is an example of a position data acquiring unit.

The smoothing-processing function 813 realizes a function equivalent to the smoothing-processing function 403 shown in FIG. 3. The smoothing-processing function 813 is an example of a smoothing-processing unit.

The correcting function 814 realizes a function equivalent to the correcting function 404 shown in FIG. 3. The correcting function 814 is an example of a correcting unit.

The display-processing function 815 has a function of generating volume data based on the multiple raw data and the smoothed position data, a function of generating 3D image data for display based on the volume data, and a function of displaying the 3D image data as a 3D image on the display 84. The display-processing function 815 is an example of a display-processing unit.

The operation of the medical image processing apparatus 80 is the same as the operation of steps ST5 to ST10 of the ultrasonic diagnostic apparatus 30 shown in FIG. 8.

According to the medical image processing apparatus 80, the multiple position data of the multiple 2D image data acquired by moving the ultrasonic probe 10 in the Z-axis direction are smoothed in the time direction, and thereby it is possible to correct the fluctuation of the imaging region in the Y-axis direction, which is caused by a change in pressure in the Y-axis direction, when the ultrasonic probe 10 is moved in the Z-axis direction. Thereby, it is possible to display appropriate 3D image data excellent in diagnostic ability.

According to at least one embodiment described above, it is possible to suppress a distortion of a display image due to a camera shake, a pulsation of a blood vessel, or the like, which is likely to occur during a moving operation of the ultrasonic probe.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
processing circuitry configured to
acquire multiple position data associated with respective multiple two-dimensional image data of ultrasonic related to multiple frames, the multiple position data each including a position consisting of coordinates in three axes and a tilt angle in three axes,
smooth, separately in three axes, the position and the tilt angle both included in the acquired position data corresponding to the acquired two-dimensional image data between the frames, and
arrange the multiple two-dimensional image data in accordance with the smoothed multiple position data to generate volume data.

2. The ultrasonic diagnostic apparatus according to claim 1, wherein
the processing circuitry is configured to acquire the multiple position data included in metadata attached to the multiple two-dimensional image data, and smooth the acquired multiple position data.

3. The ultrasonic diagnostic apparatus according to claim 2, wherein
the processing circuitry is configured to correct the multiple position data before smoothing that is attached to the multiple two-dimensional image data with multiple position data after smoothing.

4. The ultrasonic diagnostic apparatus according to claim 1, wherein
the processing circuitry is configured to acquire the multiple position data from a table in which multiple position data are associated with respective multiple two-dimensional image data, and smooth the acquired multiple position data.

5. The ultrasonic diagnostic apparatus according to claim 1, wherein
the processing circuitry is configured to average each of the acquired multiple position data and multiple position data associated with the multiple two-dimensional image data of the frames before and after thereof, thereby to smooth the acquired multiple position data.

6. The ultrasonic diagnostic apparatus according to claim 5, wherein
the processing circuitry is configured to apply a simple averaging filter to each of the acquired multiple position data and multiple position data associated with the multiple two-dimensional image data of the frames before and after thereof.

7. The ultrasonic diagnostic apparatus according to claim 5, wherein
the processing circuitry is configured to apply a weighted averaging filter to each of the acquired multiple position data and multiple position data associated with the multiple two-dimensional image data of the frames before and after thereof, the weighted averaging filter performing the weighted averaging in accordance with intervals from the each of the acquired multiple position data.

8. The ultrasonic diagnostic apparatus according to claim 7, wherein
the processing circuitry is configured to set the weighted averaging filter as a Gaussian filter, and smooth the acquired multiple position data.

9. A medical image processing apparatus comprising:
processing circuitry configured to
acquire multiple position data associated with respective multiple two-dimensional image data of ultrasonic related to multiple frames, the multiple position data each including a position consisting of coordinates in three axes and a tilt angle in three axes,
smooth, separately in three axes, the position and the tilt angle both included in the acquired position data corresponding to the acquired two-dimensional image data between the frames, and
arrange the multiple two-dimensional image data in accordance with the smoothed multiple position data to generate volume data.

10. A non-transitory computer readable medium storing a program which when executed by a computer performs the functions of:
acquiring multiple position data associated with respective multiple two-dimensional image data of ultrasonic related to multiple frames, the multiple position data each including a position consisting of coordinates in three axes and a tilt angle in three axes, smoothing, separately in three axes, the position and the tilt angle both included in the acquired position data corresponding to the acquired two-dimensional image data between the frames, and
arranging the multiple two-dimensional image data in accordance with the smoothed multiple position data to generate volume data.

* * * * *